(12) United States Patent
Christophers et al.

(10) Patent No.: US 7,419,781 B1
(45) Date of Patent: Sep. 2, 2008

(54) HUMAN ANTIBIOTIC PROTEINS

(75) Inventors: Enno Christophers, Kiel (DE); Jurgen Harder, Kiel (DE); Jens Schroder, Blumenthal (DE)

(73) Assignee: Planton GmbH, Kiel (DE)

( * ) Notice: Subject to any disclaimer, the term of this patent is extended or adjusted under 35 U.S.C. 154(b) by 0 days.

(21) Appl. No.: 09/868,569

(22) PCT Filed: Feb. 1, 2000

(86) PCT No.: PCT/EP00/00776

§ 371 (c)(1),
(2), (4) Date: Jan. 22, 2002

(87) PCT Pub. No.: WO00/46245

PCT Pub. Date: Aug. 10, 2000

(30) Foreign Application Priority Data

Feb. 1, 1999 (DE) ................. 199 05 128
Oct. 8, 1999 (DE) ................. 199 49 436

(51) Int. Cl.
*C12Q 1/68* (2006.01)
*A61K 39/00* (2006.01)
*C07H 21/04* (2006.01)
*C12P 21/04* (2006.01)
*C07K 14/00* (2006.01)

(52) U.S. Cl. ............ 435/6; 530/300; 530/350; 424/184.1; 424/190.1; 435/69.1; 435/69.7; 526/23.5; 526/23.7

(58) Field of Classification Search ............ 435/6, 435/69.1, 69.7; 530/300, 350; 536/23.5, 536/23.7; 424/184.1, 190.1
See application file for complete search history.

(56) References Cited

FOREIGN PATENT DOCUMENTS

| EP | 0943679 | 9/1999 |
|---|---|---|
| WO | 9415561 | 7/1994 |
| WO | WO 98/55600 | 12/1998 |
| WO | 9913080 | 3/1999 |

OTHER PUBLICATIONS

Snyder et al, Text book on Molecular Genetics of Bacteria, American Society for Microbiology 1997.*
Gerhold et al.[BioEssays, vol. 18, No. 12, pp. 973 981(1996)]; Wells et al.[Journal of Leukocyte Biology, vol. 61, No. 5, pp. 545 550 (1997)]; Russell et al.[Journal of Molecular Biology, vol. 244, pp. 332 350 (1994)].*
Rudinger et al, in "Peptide Hormones", edited by Parsons, J.A., University Park Press, Jun. 1976.*
Burgess et al., The Journal of Cell Biology, 111:2129 2138, 1990.*
Lazar et al., Molecular and Cellular Biology, 8(3):1247 1252, 1988.*
Jobling et al. (Mol. Microbiol., 1991, 5(7):1755 67.*
Proc. Natl. Acad. Sci. USA, vol. 88, S. 3952-3956, 1991.
Rosenberg H F et al: "Molecular Cloning and Characterization of a Novel Human Ribonuclease (RNASE K6): Increasing Diversity in the Enlarging Ribonuclease Gene Family" Nucleic Acids Research,GB,Oxford University Press, Surrey, Bd. 24, Nr. 18, 1996, Seiten 3507-3513, XP002074516 ISSN: 0305-1048.
J-M Schroeder: "Identification and structural characterization of chemokines in lesional skin material of patients with inflammatory skin disease" Methods in Enzymology, Bd. 268, 1997, Seiten 266-296, XP000864768 San Diego US in der Anmeldung erwaehnt.
Harder J: "A Peptide Antibiotic From Human Skin" Nature,GB,MacMillan Journals Ltd., London, Bd. 387, (Jun. 26, 1997), Seite 861 XP002072639 ISSN: 0028-0836 in der Anmeldung erwaehnt.

* cited by examiner

*Primary Examiner*—Shanon A. Foley
*Assistant Examiner*—Padma v Baskar
(74) *Attorney, Agent, or Firm*—Clark & Elbing LLP

(57) ABSTRACT

The invention relates to proteins, notably SAP-2 and SAP-3, having an antibiotic action. The invention also relates to a method for purifying certain antimicrobial proteins, as well as to a use of said antimicrobial proteins for antibiotic therapy or to a use of cells which were transfected with a DNA which codes for the proteins provided for in the invention.

7 Claims, No Drawings

```
                        SEQUENCE LISTING

<160> NUMBER OF SEQ ID NOS: 8

<210> SEQ ID NO 1
<211> LENGTH: 128
<212> TYPE: PRT
<213> ORGANISM: Homo sapiens

<400> SEQUENCE: 1

Lys Pro Lys Gly Met Thr Ser Ser Gln Trp Phe Lys Ile Gln His Met
  1               5                  10                  15

Gln Pro Ser Pro Gln Ala Cys Asn Ser Ala Met Lys Asn Ile Asn Lys
             20                  25                  30

His Thr Lys Arg Cys Lys Asp Leu Asn Thr Phe Leu His Glu Pro Phe
         35                  40                  45

Ser Ser Val Ala Ala Thr Cys Gln Thr Pro Lys Ile Ala Cys Lys Asn
     50                  55                  60

Gly Asp Lys Asn Cys His Gln Ser His Gly Pro Val Ser Leu Thr Met
 65                  70                  75                  80

Cys Lys Leu Thr Ser Gly Lys Tyr Pro Asn Cys Arg Tyr Lys Glu Lys
                 85                  90                  95

Arg Gln Asn Lys Ser Tyr Val Val Ala Cys Lys Pro Pro Gln Lys Lys
            100                 105                 110

Asp Ser Gln Gln Phe His Leu Val Pro Val His Leu Asp Arg Val Leu
        115                 120                 125

<210> SEQ ID NO 2
<211> LENGTH: 45
<212> TYPE: PRT
<213> ORGANISM: Homo sapiens

<400> SEQUENCE: 2

Gly Ile Ile Asn Thr Leu Gln Lys Tyr Tyr Cys Arg Val Arg Gly Gly
  1               5                  10                  15

Arg Cys Ala Val Leu Ser Cys Leu Pro Lys Glu Glu Gln Ile Gly Lys
             20                  25                  30
```

Cys Ser Thr Arg Gly Arg Lys Cys Cys Arg Arg Lys Lys
        35                  40                  45

<210> SEQ ID NO 3
<211> LENGTH: 156
<212> TYPE: PRT
<213> ORGANISM: Homo sapiens

<400> SEQUENCE: 3

Met Ala Pro Ala Arg Ala Gly Phe Cys Pro Leu Leu Leu Leu Leu
 1               5                  10                  15

Leu Gly Leu Trp Val Ala Glu Ile Pro Val Ser Ala Lys Pro Lys Gly
            20                  25                  30

Met Thr Ser Ser Gln Trp Phe Lys Ile Gln His Met Gln Pro Ser Pro
        35                  40                  45

Gln Ala Cys Asn Ser Ala Met Lys Asn Ile Asn Lys His Thr Lys Arg
    50                  55                  60

Cys Lys Asp Leu Asn Thr Phe Leu His Glu Pro Phe Ser Ser Val Ala
 65                 70                  75                  80

Ala Thr Cys Gln Thr Pro Lys Ile Ala Cys Lys Asn Gly Asp Lys Asn
                85                  90                  95

Cys His Gln Ser His Gly Pro Val Ser Leu Thr Met Cys Lys Leu Thr
            100                 105                 110

Ser Gly Lys Tyr Pro Asn Cys Arg Tyr Lys Glu Lys Arg Gln Asn Lys
        115                 120                 125

Ser Tyr Val Val Ala Cys Lys Pro Pro Gln Lys Lys Asp Ser Gln Gln
    130                 135                 140

Phe His Leu Val Pro Val His Leu Asp Arg Val Leu
145                 150                 155

<210> SEQ ID NO 4
<211> LENGTH: 67
<212> TYPE: PRT
<213> ORGANISM: Homo sapiens

<400> SEQUENCE: 4

Met Arg Ile His Tyr Leu Leu Phe Ala Leu Leu Phe Leu Phe Leu Val
 1               5                  10                  15

Pro Val Pro Gly His Gly Gly Ile Ile Asn Thr Leu Gln Lys Tyr Tyr
            20                  25                  30

Cys Arg Val Arg Gly Gly Arg Cys Ala Val Leu Ser Cys Leu Pro Lys
        35                  40                  45

Glu Glu Gln Ile Gly Lys Cys Ser Thr Arg Gly Arg Lys Cys Cys Arg
    50                  55                  60

Arg Lys Lys
 65

<210> SEQ ID NO 5
<211> LENGTH: 384
<212> TYPE: DNA
<213> ORGANISM: Homo sapiens

<400> SEQUENCE: 5
aagcccaagg gcatgaccct catcacagtgg tttaaaattc agcacatgca gcccagccct      60
caagcatgca actcagccat gaaaaacatt aacaagcaca caaaacggtg caaagacctc     120
aacaccttcc tgcacgagcc tttctccagt gtggccgcca cctgccagac ccccaaaata     180

```
-continued gcctgcaaga atggcgataa aaactgccac cagagccacg ggcccgtgtc cctgaccatg     240
tgtaagctca cctcagggaa gtatccgaac tgcaggtaca aagagaagcg acagaacaag     300
tcttacgtag tggcctgtaa gcctccccag aaaaaggact ctcagcaatt ccacctggtt     360
cctgtacact tggacagagt cctt                                            384

<210> SEQ ID NO 6
<211> LENGTH: 135
<212> TYPE: DNA
<213> ORGANISM: Homo sapiens

<400> SEQUENCE: 6
ggaatcataa acacattaca gaaatattat tgcagagtca gaggcggccg gtgtgctgtg      60
ctcagctgcc ttccaaagga ggaacagatc ggcaagtgct cgacgcgtgg ccgaaaatgc     120
tgccgaagaa agaaa                                                     135

<210> SEQ ID NO 7
<211> LENGTH: 468
<212> TYPE: DNA
<213> ORGANISM: Homo sapiens

<400> SEQUENCE: 7
atggcaccgg ccagagcagg attctgcccc cttctgctgc ttctgctgct ggggctgtgg      60
gtggcagaga tcccagtcag tgccaagccc aagggcatga cctcatcaca gtggtttaaa     120
attcagcaca tgcagcccag ccctcaagca tgcaactcag ccatgaaaaa cattaacaag     180
cacacaaaac ggtgcaaaga cctcaacacc ttcctgcacg agcctttctc cagtgtggcc     240
gccacctgcc agaccccaa aatagcctgc aagaatggcg ataaaaactg ccaccagagc     300
cacgggcccg tgtccctgac catgtgtaag ctcacctcag ggaagtatcc gaactgcagg     360
tacaaagaga agcgacagaa caagtcttac gtagtggcct gtaagcctcc ccagaaaaag     420
gactctcagc aattccacct ggttcctgta cacttggaca gagtcctt                 468

<210> SEQ ID NO 8
<211> LENGTH: 201
<212> TYPE: DNA
<213> ORGANISM: Homo sapiens

<400> SEQUENCE: 8
atgaggatcc attatcttct gtttgctttg ctcttcctgt ttttggtgcc tgtcccaggt      60
catggaggaa tcataaacac attacagaaa tattattgca gagtcagagg cggccggtgt     120
gctgtgctca gctgccttcc aaaggaggaa cagatcggca gtgctcgac gcgtggccga     180 aaatgctgcc gaagaaagaa a                                              201
```

HUMAN ANTIBIOTIC PROTEINS

The invention relates to proteins/peptides (proteins), which have an antibiotic action. In addition, the invention comprises a process for the purification of certain antibiotic proteins. The invention also relates to a use of the proteins for antibiotic treatment or to a use of cells that were transfixed with a DNA that codes for the antibiotic proteins.

PRIOR ART

Pathogenic microorganisms are usually found on the surfaces of epithelial cells. The microorganisms adhere to the cells and are reproduced. They also sometimes penetrate the deeper tissue layers. Since the immunological response to these pathogenic microorganisms sets in slowly, it is not surprising that the epithelial cells have a defense to take action against the microorganisms with the aid of secreted antimicrobial substances. Some of these substances lead to malnutrition in the microorganisms; others kill the microorganisms by the structures of the microorganisms being destroyed.

The epithelial cells of mammals are not infected in the normal way. Nevertheless, the skin surface is densely populated by bacteria and fungi. In this case, these are skin-specific microorganisms that, if they are under control, are not pathogenic.

The first known epithelial β defensin, which protects the trachea of bovines, is TAP, which has 64 amino acids. (D. G. ZASLOFF et al. (1991) Proc. Natl. Acad. Sci. USA, Vol. 88, pp. 3952-3956). This bovine TAP has an antibacterial action against *E. coli*, *Klebsiella pneumoniae*, *Staphylococcus aureus* and *Pseudomonas aeruginosa* at a minimum inhibition concentration of 12-50 µg/ml. *Candida albicans* is also destroyed. In this case, this is a protein that is expressed in a tissue-specific manner.

Another β-defensin protects the tongues of bovine animals, namely LAP, which is highly homologous to TAP. (B. S. SCHONWETTER et al. (1995) Science Vol. 267, pp. 1645-1648).

Not until 1995 was the first human β-defensin found, which is named hBD-1. (K. W. BENSCH et al. (1995) FEBS Lett., Vol. 368, pp. 331-335). hBD-1 thus has an antibacterial action again gram-negative bacteria at a concentration of 60 to 500 µg/ml. (M. GOLDMAN et al. (1997) Cell. Vol. 88, pp. 553-560). hBD-1 is expressed in a dominant manner in the kidneys, but other epithelial tissues also secrete hBD-1.

Regardless of these studies, there was interest in what normally keeps the skin healthy and why the skin is seldom infected. The second β-defensin that was isolated in humans was the hBD-2, which consists of 41 amino acids. (J. HARDER et al. (1997) Nature, Vol. 387, p. 861). hBD-2 acted very effectively against gram-negative bacteria with an $LD_{90}$ of 10 µg/ml; conversely, in the case of gram-positive bacteria, the value exceeds 100 µg/ml. The hBD-2 is an inducible peptide, which can itself be induced by some heat-inactivated bacteria.

Another human antibiotic protein is the ALP, a protease inhibitor (J. A. KRAMPS et al. (1988) Biol. Chem. Hoppe Seyler, Vol. 369, pp. 83-87), which is produced by keratinocytes and directed against several bacteria and fungi.

The attacks of antibiotic proteins are very different. Interaction with the membranes of the microorganisms are common. Lipophilic structures of many antibiotic proteins and the defensins speak for intercalation in the membranes or penetration of the membranes. The antimicrobial proteins and peptides have a toxic action only in the microorganisms themselves.

OBJECTS AND SOLUTION

The object of the invention is to offer additional human, antibiotic proteins and their derivatives, which can be used effectively against microorganisms, especially against gram-negative and gram-positive bacteria, against fungi and against viruses.

Sequences of Mature Proteins

The object is achieved by at least one protein,
a) which has one of the following sequences as an active, mature protein/peptide (protein):
  (i) SEQ ID NO: 1 (Sequence Protocol No. 1) (SAP-2); or
  (ii) SEQ ID NO: 2 (Sequence Protocol No. 2) (SAP-3);
or
b) which has allelic modifications of one of the amino acid sequences that are mentioned above under a) as an active, mature protein, whereby at least one amino acid of the amino acid sequence is substituted, deleted, or inserted, without in this case significantly affecting the activity of the active protein,
or
c) which has post-translational modifications of one of the sequences under a) and b) as an active, mature protein, and these modifications do not significantly affect the activity of the active protein.

A protein according to the invention that has an antimicrobial and/or antibiotic action is advantageous.

A protein according to the invention that has an antimicrobial or antibiotic action and that has a mobility of 6 kDa in the SDS-gel electrophoresis is advantageous.

More preferred is a protein according to the invention that has an antibiotic activity against *Escherichia coli* or *Staph. aureus* at a concentration of less than 100 µg/ml.

In the literature, the designation SAP-2 is to be replaced by RNase 7 in the future, and the term SAP-3 is to be substituted by hBD-3 in the future.

Very preferred is a protein according to the invention that is a protein that is provided with the human amino acid sequence (cf. SEQ ID NO: 1 to 2).

Regarding SEQ ID NO: 1

All allelic modifications that comprise the substitutions, the deletions and/or the insertions of up to 30 amino acids belong to the group of proteins of SEQ ID NO: 1 according to the invention. Preferred are deletions, substitutions and/or insertions of up to 20 amino acids, and more preferred are those of up to 10 amino acids; most preferred are the deletions, substitutions and/or insertions of one, two, three, four, five, six, seven, eight or nine amino acids. The allelic modifications are not limited to the naturally occurring alleles, rather changes of the amino acid sequence that are produced in the laboratory (not occurring in nature itself) are also possible.

Regarding SEQ ID NO: 2

All allelic modifications that comprise the substitutions, the deletions and/or the insertions of up to 10 amino acids belong to the group of proteins of SEQ ID NO: 2 according to the invention. Preferred are deletions, substitutions and/or insertions of up to 6 amino acids, and more preferred are those of up to 4 amino acids; most preferred are deletions, substitutions and/or insertions of one, two or three amino acids. The above-mentioned broadening to changes that comprise synthetically producible changes in addition to naturally occurring changes also applies here.

Sequences of Nature Proteins with Signal Sequence

The object is also achieved by at least one protein, which comprises a signal sequence and a mature protein according to the invention,
- d) whereby the protein has one of the following sequences:
    - (i) SEQ ID NO: 3 (PreSAP-2); or
    - (ii) SEQ ID NO: 4 (PreSAP-3);
- or
- e) whereby the protein has allelic modifications of one of the amino acid sequences that are mentioned above under d), whereby at least one amino acid of the amino acid sequence is substituted, deleted or inserted, without in this case significantly affecting the activity of the mature active protein,
- or
- f) whereby the protein has post-translational modifications of one of the sequences under d) and e), which do not significantly affect the activity of the active mature protein.

Regarding SEQ ID NO: 3

All allelic modifications that comprise the substitutions, the deletions and/or the insertions of up to 35 amino acids belong to the group of proteins of SEQ ID NO: 3 according to the invention. Preferred are deletions, substitutions and/or insertions of up to 23 amino acids, and more preferred are those of up to 12 amino acids; most preferred are deletions, substitutions and/or insertions of one, two, three, four, five, six, seven, eight or nine amino acids. The allelic modifications are not limited to the naturally occurring alleles, but rather changes of the amino acid sequence that are produced in the laboratory (not occurring in nature itself) are also possible.

Regarding SEQ ID NO: 4

All allelic modifications that comprise the substitutions, the deletions and/or the insertions of up to 13 amino acids belong to the group of proteins of SEQ ID NO: 4 according to the invention. Preferred are deletions, substitutions and/or insertions of up to 8 amino acids, and more preferred are those of up to 6 amino acids; most preferred are deletions, substitutions and/or insertions of one, two, three, four or five amino acids. The above-mentioned broadening to changes that comprise synthetically producible changes in addition to naturally occurring changes also applies here.

Most preferred is a protein according to the invention that is a recombinant protein. In this case, the proteins can be glycosylated if this is a SAP-2 or a variant thereof.

The proteins according to the invention comprise the mature proteins and the corresponding precursor proteins, which consist of a signal sequence and the sequence of the mature protein. In this case, the signal sequence presupposes the sequence of the mature protein. The mature protein begins with the above-mentioned N-terminal sequence under item a). The signal sequence is necessary for the penetration of the endoplasmatic reticulum.

It is also possible to synthesize protective groups, which are known from peptide chemistry, at the N-terminus and/or C-terminus.

The protective group of the N-terminus can consist of:

Alkyl, aryl, alkylaryl, aralkyl, alkylcarbonyl or arylcarbonyl groups with 1 to 10 carbon atoms; preferred are naphthoyl, naphthylacetyl, naphthylpropionyl, benzoyl groups or an acyl group with 1 to 7 carbon atoms.

The protective group of the C-terminus can consist of:

A substituted or unsubstituted alkoxy or aryloxy group with 1 to 10 carbon atoms or an amino group.

Other protective groups—both for the N-terminus and for the C-terminus—are described in Houben-Weyl (1974) Georg Thieme Verlag, 4th Edition. The description of the protective groups in the cited bibliography is part of the disclosure.

The sequence of the protein according to the invention can be connected with other framework-amino acid sequences (analogously to the definition of "framework" in antibodies) at the N-terminal and/or C-terminal end instead of a protective group. These other framework-amino acid sequences are not essential for the bonding of the protein according to the invention, but they can be vehicles of other functions, and thus include, for example, chelates or else cytostatic or cytotoxic sequences. Such framework-amino acid sequences occur in nature. These may be, for example, the sequences of the variable area of an antibody that are arranged between the hypervariable areas. These sequences are referred to as "framework" (framework sequences). As framework-amino acid sequences, non-cleaved partial signal sequences of a secreted eukaryotic protein are also known, whereby the protein is expressed in a bacterium. At times, such signal sequences have no effect on the function of the subsequent protein. It is also possible to couple proteins according to the invention behind one another, whereby framework-amino acid sequences are arranged between the individual sequences.

To decide in individual cases whether a certain protein according to the invention with at least one framework-amino acid sequence and/or at least one protective group is to be included in the subject of the invention, a comparison can be made between
- (i) this protein with a framework-amino acid sequence and/or with a protective group, and
- (ii) the same protein without a framework-amino acid sequence and without a protective group.

In this case, the two molecules that are compared should have essentially the same functions of inhibition or binding.

cDNA OR DNA that Code for the Proteins According to the Invention

The invention also comprises a cDNA or DNA,
- aa) whereby the cDNA or DNA codes one of the following amino acid sequences:
    - (i) SEQ ID NO: 1 (SAP-2);
    - (ii) SEQ ID NO: 2 (SAP-3);
    - (iii) SEQ ID NO: 3 (PreSAP-2); or
    - (iv) SEQ ID NO: 4 (PreSAP-3)
- or
- bb) whereby the cDNA or DNA codes allelic modifications of one of the amino acid sequences under aa), in which at least one amino acid of the amino acid sequence is substituted, deleted or inserted, without in this case significantly affecting the activity of the active protein.

cDNA and DNA, which code a mature protein according to the invention, are preferred.

The allelic modifications have been defined above under the item "Sequences of the Mature Proteins."

Regarding SEQ ID NO: 1 and 3

All allelic modifications that comprise the substitutions, the deletions and/or the insertions of up to 90 nucleotides belong to the group of DNAs of SEQ ID NO: 1 and 3 according to the invention. Preferred are deletions, substitutions and/or insertions of up to 60 nucleotides, and more preferred are those of up to 30 nucleotides; most preferred are deletions, substitutions and/or insertions of one, two, three, four, five, six, seven, eight or nine or 10 to 29 nucleotides. The allelic modifications are not limited to the naturally occurring alleles, but rather changes of the amino acid sequence that are produced in the laboratory (not occurring in nature itself) are also possible.

Regarding SEQ ID NO: 2 and 4

All allelic modifications that comprise the substitutions, the deletions and/or the insertions of up to 30 nucleotides belong to the group of DNAs of SEQ ID NO: 2 and 4 according to the invention. Preferred are deletions, substitutions and/or insertions of up to 18 nucleotides, and more preferred are those of up to 12 nucleotides; most preferred are deletions, substitutions and/or insertions of one, two, or three or 4 to 11 nucleotides. The above-mentioned broadening to changes that comprise synthetically producible changes in addition to naturally occurring changes also applies here.

In addition, the invention comprises a cDNA or DNA,
cc) whereby the cDNA or DNA has one of the following nucleotide sequences:
(i) SEQ ID NO: 5 (cDNA-SAP-2)
(ii) SEQ ID NO: 6; (cDNA-SAP-3);
or
dd) whereby the cDNA or DNA has an allelic modification of one of the nucleotide sequences under cc), whereby at least one nucleotide is substituted, deleted or inserted, without in this case significantly affecting the activity of the protein, which is coded by the allelic modification of the nucleotide sequence under cc).

Regarding SEQ ID NO: 5

All allelic modifications that comprise the substitutions, the deletions and/or the insertions of up to 90 nucleotides belong to the group of DNAs of SEQ ID NO: 5 according to the invention. Preferred are deletions, substitutions and/or insertions of up to 60 nucleotides, and more preferred are those of up to 30 nucleotides; most preferred are deletions, substitutions and/or insertions of one, two, three, four, five, six, seven, eight or nine or 10 to 29 nucleotides. The allelic modifications are not limited to the naturally occurring alleles.

Regarding SEQ ID NO: 6

All allelic modifications that comprise the substitutions, the deletions and/or the insertions of up to 30 nucleotides belong to the group of DNAs of SEQ ID NO: 6 according to the invention. Preferred are deletions, substitutions and/or insertions of up to 18 nucleotides, and more preferred are those of up to 12 nucleotides; most preferred are deletions, substitutions and/or insertions of one, two, or three or 4 to 11 nucleotides. The above-mentioned broadening to changes that comprise synthetically producible changes in addition to naturally occurring changes also applies here.

Preferred are cDNA and DNA, which code a protein according to the invention.

Another embodiment of the invention comprises a cDNA or DNA,
ee) whereby the cDNA or DNA has one of the following nucleotide sequences:
(i) SEQ ID NO: 7 (cDNA-PreSAP-2) or
(ii) SEQ ID NO: 8 (cDNA-PreSAP-3),
or
ff) whereby the cDNA or DNA has an allelic modification of one of the nucleotide sequences under ee), whereby at least one nucleotide is substituted, deleted or inserted, without in this case significantly affecting the activity of the protein, which is coded by the allelic modification of the nucleotide sequence under ee).

cDNA and DNA, which code a preprotein according to the invention, are preferred.

Regarding SEQ ID NO: 7

All allelic modifications that comprise the substitutions, the deletions and/or the insertions of up to 90 nucleotides belong to the group of DNAs of SEQ ID NO: 5 according to the invention. Preferred are deletions, substitutions and/or insertions of up to 60 nucleotides, and more preferred are those of up to 30 nucleotides; most preferred are deletions, substitutions and/or insertions of one, two, three, four, five, six, seven, eight or nine or 10 to 29 nucleotides. The allelic modifications are not limited to the naturally occurring alleles.

Regarding SEQ ID NO: 8

All allelic modifications that comprise the substitutions, the deletions and/or the insertions of up to 30 nucleotides belong to the group of DNAs of SEQ ID NO: 6 according to the invention. Preferred are deletions, substitutions and/or insertions of up to 18 nucleotides, and more preferred are those of up to 12 nucleotides; most preferred are deletions, substitutions and/or insertions of one, two, or three or 4 to 11 nucleotides. The above-mentioned broadening to changes that comprise synthetically producible changes in addition to naturally occurring changes also applies here.

All DNA constructs also then include the listed sequences according to the invention, if such nucleotides are exchanged, which code the same amino acid based on the degenerated code. The exchange of such nucleotides is obvious, and the corresponding amino acids are disclosed in any biochemistry textbook. (R. KNIPPERS, 1982, 3rd Edition, Molekulare Genetik [Molecular Genetics], Georg Thieme Verlag)

The allelic modifications have been defined above.

If the activity of the protein is indicated to determine whether the allelic modification is included under the group of the proteins according to the invention, the mature protein is thus always to be measured, even if the signal sequence is also indicated. If the signal sequence should be indicated, the function is always to be measured at the protein, which is obtained after the signal sequence is removed.

The activity of the proteins according to the invention is measured in terms of its function, which can be an antibiotic action, an antimicrobial action and/or the binding to antibodies or binding molecules that are directed against the mature human protein.

The invention also comprises binding molecules (for example peptides or derivatives thereof), single-chain proteins, antibodies or fragments of antibodies, which specifically detect domains on the mature protein according to the invention. If the purified protein according to the invention is present, it is easily possible for one skilled in the art to produce monoclonal antibodies. In this case, the known method of Köhler and Milstein and its extensions are used. In particular, in conventional methods, a mouse is immunized several times with the purified protein, the splenocytes are removed and fused with suitable tumor cells. The hybrids are then selected. The binding molecules can be used as a diagnostic agent to determine, for example, whether the respective patient suffers from a deficiency or a variant of the proteins according to the invention.

The proteins of the invention can be isolated from, for example, horny scales of psoriasis patients. Purification is done according to the examples. The proteins have the above-described amino acid sequences. They have a molecular weight of about $20,000 \pm 2,000$ with SAP-2 and $6,000 \pm 2,000$ with SAP-3 (see examples). The isoelectric point lies in a range of pH 8.5 to 10.5, if the method that is described in the example is used.

The proteins according to the invention can have a natural origin. The proteins are obtained by being harvested and worked up according to the examples. The horny scale supernatant is purified, and the proteins according to the invention are isolated and concentrated. All concentration stages of the isolation and the purification are part of the invention. Preferred are the concentration stages of isolation and purification, in which the proteins according to the invention can be used for pharmaceutical purposes. Purifications of 50% of the proteins relative to the total protein thus are achieved; preferred are 85%, more preferred 95% and most preferred 99% of the proteins relative to the total protein.

It is also possible to produce the proteins according to the invention synthetically. This includes protein synthesis according to J. M. SEWART and J. D. YOUNG, San Francisco, 1969 and J. MEIENHOFER, Hormonal Proteins and Peptides, Vol. 2, p. 46, Academic Press (New York), 1973 and E. SCHODER and K. LUBKE, The Peptides, Vol. 1, Academic Press (New York) 1965. The citations are part of the disclosure.

The synthetically produced proteins also include the recombinant proteins, which are produced according to known processes. Depending on the host organism, the proteins according to the invention (with SAP-2) can be glycosylated or, if they are synthesized in prokaryotes, unglycosylated.

The function of toxicity against microorganisms can be determined in various testing systems. In the examples, standard testing procedures are described. (Cf. SELSTED et al. (1993) J. Biol. Chem., Vol. 268, pp. 6641-6648 and GANZ et al. (1985) J. Clin. Invest. Vol. 76, pp. 1427-1435)

The proteins of the invention have an antibiotic action against microorganisms, especially against the gram-negative and gram-positive families, in this case preferably against the E. coli and Staphylococcus aureus types.

The testing systems are described in detail in Example 3.

Vectors with the DNA According to the Invention

Another part of the invention is a vector that contains a cDNA or DNA according to the invention, also a suitable promoter and optionally a suitable enhancer. A signal sequence can also be comprised. Vectors are described in more detail in European publications EP 0 480 651, EP 0 462 632 and EP 0 173 177.

Another embodiment of the invention consists in a eukaryotic or prokaryotic host cell, which is transformed with a vector according to the invention.

The invention also comprises a process for the production of a protein according to the invention with use of a host cell according to the invention, with the steps:

Cultivation of the host cell, accumulation of the protein, and purification of the protein.

The invention also comprises a process for synthesizing one of the proteins according to the invention, whereby the proteins are synthesized according to the solid-phase method or according to the liquid-phase method.

The process in which the proteins according to the invention are produced has the following stages:

The carboxyl end of an amino acid that is to be coupled, its amino groups and optionally functional groups of the side chain carry a protective group, reacts with the free amino end of the amino acid that is to be coupled or the protein fragment that is to be coupled in the presence of a condensation reagent, and in the case of a non-terminal amino acid, the α-amino protective group is then cleaved off from the coupled amino acid, and other amino acids are coupled to the protein chain that is to be synthesized according to the two steps that are described above, or in the case of a terminal amino acid, the α-amino protective group is optionally then cleaved off from the coupled amino acid and after the last amino acid is coupled in the case of the solid-phase method, the protein is cleaved off from the solid phase.

Allelic Modifications

Most deletions, insertions and substitutions do not appear to result in any drastic change in the characteristics of the protein of the invention. Since it is difficult to indicate the exact effects of a substitution, a deletion or an insertion beforehand, the function of the altered protein must be compared with the function of the protein according to the invention. The methods that are to be used for this purpose are indicated in the examples. As a standard, the protein according to SEQ ID NO: 1 to 2 is used, and the protein that is purified according to Example 1 or 2 and also the purification methods of Example 1 or 2 are used for the comparison protein.

The genetic code is degenerated, i.e., most amino acids are coded by more than one codon that consists of three nucleotides. Several allelic modifications on the plane of the nucleotides therefore do not lead to an alteration of the amino acid sequence. Allelic modifications therefore take place in particular on the plane of DNA and can have a secondary effect on the amino acid sequence.

The cDNA or DNA sequences, which code the proteins according to the invention, can be modified according to conventional techniques to produce variants of the proteins according to the invention, which essentially have the same activity as the proteins of the invention that are described and characterized. In this case, the activity is measured as it is described in the examples. Such a complete homology testing is described in CUNNINGHAM et al. (1989) Science, Vol. 243, p. 1330, and O'DOWD et al. (1988), J. Biol. Chem., Vol. 263, p. 15985.

Amino acids can be substituted, whereby the amino acids can be substituted in their positions with a protein or peptide mapping, whereby then the activity of the modification is measured. In this case, substitutions that are determined by experiment are possible, which is not easily predictable owing to the chemical structure of the side chains.

The mutations are defined by the homology (similarity) of two proteins pending comparison. The term homology comprises similar amino acids and gaps in the sequences of the amino acids (homology=similarity). The proteins according to the invention have amino acid sequences, which have a homology of at least 80%, preferably 90%, more preferably 95% and most preferably 98% of the structures according to the invention, as they are defined by the sequences under SEQ ID NO: 1 to 2 or SEQ ID NO: 3 and 4 and as they are also obtained after purification according to the examples.

Sequences of proteins can be simply changed. In this case, the amino acids are exchanged in their respective positions.

At the same time, it is necessary to study the function of the thus obtained sequences. The amino-acid exchange can be carried out according to two different methods.

Each position of a protein is replaced in succession by alanine. Then, the function of the molecule that is modified in each case by alanine is measured. If the measured value deviates from that of the standard protein, this amino acid at this position of the protein, on which an alanine is now arranged, is essential for the function. To this end, a map of the protein, from which the conservative positions and the positions that are accessible to a variation are indicated, is produced.

Another method consists in exchanging each position or essential positions of a protein for all 20 natural amino acids. Then, the function is tested by all of these modifications. The method is described in Ronald FRANK (1992) Spot Synthesis: Easy Technique for the Positionally Addressable, Parallel Chemical Synthesis on a Membrane Support. Tetrahedron Vol. 48, No. 42, pp. 9217-9232.

Both methods are especially suitable for peptides, since the latter are produced with the solid-phase synthesis. Nevertheless, these methods can easily also be transferred to proteins for one skilled in the art, whereby the proteins are synthesized in cells. To this end, an alteration of the DNA is essential, which can take place specifically, however, with the present techniques.

The process for modifying the amino-acid sequence can be explained as follows:
(a) At least one amino acid in the sequence of the protein is replaced by a natural amino acid or else optionally by an amino acid that is not natural.
(b) The modified protein is tested after each substitution on the antibiotic function relative to microorganisms, and the most antibiotic proteins are selected.
(c) In another step, the most antibiotic proteins are run at least in another cycle according to items (a) and (b).

The result of such a modification can be a protein that only has some parts in common with the original sequence.

As mentioned above, the invention also comprises modifications of the DNA or cDNA. These modified sequences hybridize under stringent conditions with the DNA sequences that code the proteins according to the invention (see sequences under aa); cc) and ee)). The cDNA- or DNA sequences have nucleotide sequences, which have an identity including shorter (up to 15 nucleotides) deletions and insertions of at least 70%, preferably 82%, more preferably 90% and most preferably 95% with the cDNA or DNA sequences according to the invention (see aa), cc) and ee)). The identity including the short (up to 15 nucleotides) deletions and insertions can be measured by hybridization, as it is described in R. KNIPPERS, Molekulare Genetik, 1982, Third Edition, Georg Thieme Verlag Stuttgart, New York. In addition, standard computer programs are known to one skilled in the art, with whose help homology can be calculated.

The invention also comprises a cDNA or DNA with at least one of the sequences of SEQ ID NO: 5 to 8, or nucleotide sequences, which hybridize with one of SEQ ID NO: 5 to 8 under selective, stringent conditions.

Stringent conditions are then present if the salts, their concentrations, the temperature of the inorganic and organic solvents are controlled in typical form, as is practiced in the established hybridization technique. Stringent temperature conditions include temperatures of at least 30° C., preferably at least 37° C., more preferably at least 45° C., still more preferably at least 55° C., still more advantageously at least 65° C. and most preferably at least 70° C. Stringent salt concentrations comprise less than 1000 mmol, preferably less than 700 mmol, more preferably less than 400 mmol, still more preferably less than 300 mmol, advantageously less than 200 mmol and most preferably 150 mmol. The combination of the parameters is more important than the reference to an individual parameter. (WETMUR et al. (1968) J. Mol. Biol., Vol. 31, p. 349)

Post-Translational Modifications

The above-mentioned post-translational modifications are defined as changes that occur during or after translation. These include the glycosylation, the formation of disulfide bridges, the chemical modifications of amino acids, thus, for example, the sulfation, which is described in connection with hirudin. (J. W. FENTON (1989) "Thrombin Interactions with Hirudin," Seminars in Thrombosis and Hemostasis, Vol. 15, pp. 265-268)

The glycosylation is a basic function of the endoplasmatic reticulum and/or the Golgi apparatus. The sequence and the branching of the oligosaccharides is formed in the endoplasmatic reticulum and altered in the Golgi apparatus. The oligosaccharides can be N-linked oligosaccharides (asparagine-linked) or O-linked oligosaccharides (serine-, threonine- or hydroxylysine-linked). The form of glycosylation depends on the producing cell type and on the type from which the corresponding cell type is derived. The extent and the type of glycosylation can be affected by substances, as it is described in European Publication EP 0 222 313. The variation of the glycosylation can alter the function of the protein.

Proteins form frequently covalent bonds within the chains. These disulfide bridges are produced between two cysteines. In this case, the protein is specifically precipitated. The disulfide bridges stabilize the three-dimensional structure of the proteins.

Isolation and Production of the Proteins According to the Invention

The invention also comprises a process for the purification of proteins according to the invention, whereby the process consists of the following steps:
(i) Extraction of proteins from natural human epithelial cells, transfixed cells or skin scales or cell cultures, which were optionally exposed to microorganisms,
(ii) Application of the extract on an affinity column with subsequent Reversed Phase HPLC and elution via a salt gradient, with acids or organic eluents,
or
(iii) Application of the extract on an HPLC column and elution with salts.

The purification is described in detail in the examples.

Preferred is a micro-mono-S-HPLC column.

The proteins are preferably purified according to Examples 1 and 2. Other isolation and purification methods are also possible, however:

Methods of Enzymology, Volume 182: Guide to Protein Purification, ed. Murray P. DEUTSCHER, Academic Press, 1990;

Protein Purification Application—A Practical Approach, ed. E. L. V. HARRIS and S. ANGEL, IRL Press, 1990;

Protein Purification, Principles and Practice, Ropert SCOPES, Springer-Verlag 1982; and Protein Purification, Principles, High Resolution Methods and Applications, ed. H.-C. JANSON and L. RYDEN, VCH Publishers 1989.

Use as Pharmaceutical Agents

The proteins according to the invention have pharmacological effects and can therefore be used as pharmaceutical active ingredients. The invention also comprises a pharmaceutical agent that contains one of the proteins according to the invention or a mixture thereof. A pharmaceutical composition, which contains one of the proteins according to the invention or a mixture of proteins according to the invention, in the presence of pharmaceutically compatible and acceptable compounds and vehicles, is also a part of the invention. The invention also comprises a pharmaceutical composition that contains one of the pharmaceutically active proteins according to the invention or mixture thereof and a pharmaceutically compatible salt or a pharmaceutically compatible vehicle.

The proteins according to the invention according to SEQ ID NO: 1 to 2 in particular show a toxic or antibiotic action with regard to microorganisms, especially with regard to the groups of gram-negative and gram-positive bacteria, preferably in the case of the *E. coli* and *St. aureus* types. Testing procedures are described in Example 3.

The test results of this in vitro test show that the proteins according to the invention can be used as pharmaceutical agents or for medical treatment. These test results can be transferred from the in vitro test system to an in vivo system, since these are established testing arrangements in the tests. The proteins of the invention can therefore be used for treatment and prevention of infections by microorganisms. The proteins of the invention can be used as an antibiotic medication in mammals, especially humans, for treating infections and/or for infection prophylaxis.

The invention additionally provides
(i) the use of one of the proteins according to the invention or mixture thereof for the production of a medication for treatment of infections that were caused by microorganisms or for prevention of such infections;
(ii) a process for treating infections that were caused by microorganisms or for prevention of such infections, said process comprises an administration of an amount of protein according to the invention, whereby the amount suppresses the disease, and whereby the amount of protein is given to a patient who requires such a medication;
(iii) a pharmaceutical composition for treating infections that were caused by microorganisms or for prevention of such infections, said treatment comprises one of the proteins according to the invention or mixture thereof and at least one pharmaceutically compatible vehicle and additive.

For this therapeutic action, different doses are suitable. They depend on, for example, the protein that is used, the host, the type of administration and the type and difficulty of the conditions that are to be treated. In general, however, satisfactory results are to be expected in animals if the daily doses comprise a range of 2 μg to 2000 μg per kg of body weight. In the case of larger mammals, for example humans, a recommended daily dose lies in the range of 2 to 2000 μg per kg of body weight, if the protein that is purified according to Example 1 or 2 is used. For example, this dose is suitably administered in partial doses up to four times daily. The daily dose in the case of prevention is a tenth of the amount that is used in the case of an infection.

The protein according to the invention is preferably locally or epithelially administered, thus also in the upper and lower air passages.

The proteins according to the invention can be administered in any commonly used method, also in the form of creams, gels, semisolid dosage forms, suspensions or inhalational solutions or inhalational powders.

This invention makes available pharmaceutical compositions that comprise one of the proteins according to the invention or mixture thereof and at least one pharmaceutically compatible vehicle or additive. Such compositions can be produced according to known processes. In this case, reference is to be made to Remington's Pharmaceutical Science, 15th Ed. Mack Publishing Company, East Pennsylvania (1980).

In addition, syngeneic or allogeneic human cells that are transfixed with DNA or cDNA according to the invention can be used as medication, by these cells being applied to the epithelial tissue or being located in the matrix of a bandage.

DEFINITIONS

"Antimicrobial" means that the proteins according to the invention
(i) inhibit and/or prevent the growth and/or the proliferation of microorganisms and/or
(ii) destroy the microorganisms or structures thereof.

"Antibiotic" means that the proteins according to the invention have an adverse effect on the normal biological function of the microorganisms, whereby this means death or destruction, as well as inhibition of growth or proliferation of the microorganisms, along with impairment of metabolic functions. Antibiotic also comprises the term antimicrobial. An antibiotic action can also be present in viruses. Antibiotic therefore also comprises antiviral.

"Antiviral" means that DNA and RNA viruses can be controlled with the aid of the proteins of the invention. In this case, various possible interventions are useful. The viruses can be influenced in their dormant forms. The adhesion phase to the host or the penetration in the host can be destroyed, and the retention or the reproduction (temperent or virulent phase) can be impaired in the host.

The proteins according to the invention can also be used for healing wounds.

"Healing wounds" means that, for example, the contraction of wounds is accelerated, that connective tissue has begun to form in the wound area, that collagen is stored. Burns can also be treated well with the proteins of the invention. In this case, a bandage can be enriched with proteins or proteins of special, especially transfixed cells can be expressed in the bandage.

"Microorganisms" comprise the prokaryotes with eubacteria and archaebacteria, fungi (mycota with myxomycetes, phycomycetes and eumycetes), plant and animal protozoan organisms and viruses.

The term "protein" comprises all lengths of amino acid sequences, thus also peptides. In this case, proteins can also consist of various chains, which are connected by covalent bonds or van der Waal's forces.

Combination with Antibiotics

The proteins according to the invention can be administered together with antibiotics, for example, from the following group: bacitracin, gramicidin, polymyxin, vancomycin, teichoplanin, aminoglycosides, penicillin, and monobactam.

Diagnostic Agent

The invention also comprises the use of at least one protein according to the invention for the production of antibodies or fragments thereof.

The invention also comprises the use of an antibody according to the invention or fragments thereof as a diagnostic agent.

In this case, the proteins according to the invention are to be detected in body tissues and bodily fluids. The detection processes can thus also be produced by coupling ligands to the proteins according to the invention.

EXAMPLES

Example 1

Extraction of SAP-2

1.1 Isolation 50 g of lesional psoriasis scales was extracted under acid conditions in the presence of ethanol and concentrated by evaporation. In this case, the process was followed that is described in J. M. SCHRÖDER, (1997) Methods in Enzymology, Vol. 288, pp. 266-296.

After diafiltration on 0.02 mol/l of sodium phosphate buffer, pH 8 and centrifuging, the supernatant was chromatographed on a bacteria-affinity column (*E. coli* or *Staph. aureus*), which had been produced by coupling heat-inactivated (70° C. over one hour) *E. coli* or *Staphylococcus aureus* bacteria to an N-hydroxy-succinimide-activated sepharose column (Pharmacia) (10×5 mm).

The column was washed first with the equilibration buffer, and then bonded proteins were eluted with an acid buffer (0.1 mol/l of glycine buffer, pH.3 with 1 mol/l of NaCl).

The eluate that contains bonded protein was diafiltered from 0.1% of aqueous trifluoroacetic acid solution and first subjected to a preparative Reversed Phase HPLC separation analogously to isolation from chemotactic peptides (cf. J. M. SCHRÖDER, (1997) Methods in Enzymology, Vol. 288 pp. 266-296). 20 µl of the respective fractions was freeze-dried, taken up in 5 µl of a 0.01 percent aqueous acetic acid solution and analyzed with the aid of a plate diffusion test system (see Example 3) (for the identification of antimicrobial or antibiotic proteins) analogously to M. E. SELSTED et al. (1993) J. Biol. Chem., Vol. 268, pp. 6641-6648 with respect to the presence of antimicrobial peptides (with *Staph. aureus* and *E. coli* as test bacteria).

Antimicrobially active proteins that were eluted with 40% acetonitrile were then subjected—analogously to the isolation of chemotactic peptides (J. M. SCHRÖDER, (1997) Methods in Enzymology, Vol. 288, pp. 266-296)—to a micro-mono S—HPLC separation with the aid of the Smart-HPLC system.

SAP-2 was eluted with 0.8 mol/l of NaCl.

A subsequent micro-reversed phase-HPLC analysis with the aid of a C-18 RP column yielded a protein peak that is eluted with 52% acetonitrile, which after SDS-gel electrophorese (performed according to the method of J. M. SCHRÖDER, (1997) Methods in Enzymology, Vol. 288, pp. 266-296), yielded an individual protein band or two bands corresponding to the mobility of about 20 kDa.

1.2. Sequencing of Fragments

Sequencing tests yielded the amino-terminal sequence with the numbering from the complete sequence

```
Pro Lys Gly Met Thr Ser Ser Gln Trp Phe Lys Ile
              5                   10
Gln His Met Gln Pro Ser Pro Gln Ala Cys Asn Ser
          15              20                  25
Ala Met Lys Asn Ile Asn Lys His Thr Lys Arg Cys
                  30              35
Lys Asp
```

The Erdman degradation of the peptide fragment yielded a sequence that corresponds to the C-terminus:

```
Asp Ser Gln Gln Phe His Leu Val Pro Val
            115                 120
His Leu Asp Arg Val Leu
            125
```

1.3. Biological Activity of SAP-2: MIC

Antimicrobial activity against *Staph aureus:* <100 µg/ml
against *E. coli* <50 µg/ml
RNase activity: 1.2 µg of SAP-2 digested about 5 µg of human RNA in one hour at 37° C.

Example 2

Extraction of SAP-3

2.1: Isolation 50 g of lesional psoriasis scales was extracted under acid conditions in the presence of ethanol and concentrated by evaporation. In this case, the process was followed that is described in J. M. SCHRÖDER, (1997) Methods in Enzymology, Vol. 288, pp. 266-296.

After diafiltration on 0.02 mol/l of sodium phosphate buffer, pH 8 and centrifuging, the supernatant was chromatographed on an anti-IL-8 affinity column, which had been produced by coupling monoclonal anti-IL-8 antibody 52E4 to an N-hydroxy-succinimide-activated sepharose column (Pharmacia) (analogously to J. M. SCHRÖDER, (1997) Methods in Enzymology, Vol. 287, pp. 216-230).

The column was washed first with the equilibration buffer, and then bonded protein was eluted with an acid buffer (0.1 mol/l of glycine buffer, pH 3 with 2 mol/l of NaCl).

The eluate that contains bonded protein was diafiltered from 0.1% of aqueous trifluoroacetic acid solution and first subjected to a preparative Reversed Phase HPLC separation analogously to the isolation of chemotactic peptides (cf. J. M. SCHRÖDER, (1997) Methods in Enzymology, Vol. 288, pp. 266-296). 20 µl of the respective fractions was freeze-dried, taken up in 5 µl of a 0.1 percent aqueous acetic acid solution and analyzed with the aid of a plate diffusion test system (see Example 3) (for the identification of antimicrobial or antibiotic proteins) analogously to M. E. SELSTED (1993) J. Biol. Chem., Vol. 268, pp. 6641-6648 with respect to the presence of antimicrobial peptides (with *Staph. aureus* or *E. coli* as test bacteria).

Antimicrobially active proteins that were eluted with 37% acetonitrile were then subjected—analogously to the isolation of chemotactic peptides (J. M. SCHRÖDER, (1977) Methods in Enzymology, Vol. 288, pp. 266-296)—to a micro-mono S—HPLC separation with the aid of the Smart-HPLC system.

SAP-3 was eluted with 0.79 mol/l of NaCl.

A subsequent micro-reversed phase-HPLC analysis with the aid of a C-18 RP column yielded a protein peak that is eluted with 38% acetonitrile, which after SDS-gel electrophorese (performed according to the method of J. M. SCHRÖDER, (1997) Methods in Enzymology, Vol. 288, pp. 266-296) yielded an individual protein band corresponding to the mobility of about 6 kDa.

2.2 Sequencing of Fragments

Sequencing tests yielded only the amino-terminal sequence:

```
Gly Ile Ile Asn Thr Leu Gln Lys Tyr Tyr Cys Arg
            5                   10
Val Arg Gly Gly Arg Cys Ala Val Leu Ser Cys Leu
        15                  20
Pro Lys Glu Glu Gln Ile Gly Lys
25                  30      32
```

2.3 Biological Activity of SAP-3: MIC

Antimicrobial activity from *Staph aureus:* <100 µg/ml from *E. coli:* <20 µg/ml

Example 3

3. Determination of Antimicrobial Activity

3.1 Cultivation of Microorganisms

The following microorganisms were used for the tests:
*Escherichia coli* (*E. coli*)—ATCC (American Type Culture Collection) No. 11303
*Pseudomonas aeruginosa*—ATCC No. 15442
*Staphylococcus aureus* (clinical isolates from the dermatological hospital of Kiel)
*Staphylococcus epidermidis* (clinical isolates from the dermatological hospital of Kiel)
*Candida albicans* (clinical isolates from the dermatological hospital of Kiel)

The microorganisms were cultivated on Trypticase-soy-broth (TSB) agar plates at 37° C. If they were not needed for a long time, they were stored at 4° C. For the tests, in each case a single colony of the corresponding microorganisms was inoculated in 40 ml of TSB medium and incubated overnight at 37° C. while being shaken (250 rpm). To quantify the microorganisms, the optical density of the overnight cultures was measured at 620 nm ($OD_{620}$), and the colony number was determined by flattening out corresponding dilution stages.

3.2 Plate Diffusion Test

To study as quickly and sensitively as possible the antimicrobial action of fractions of the individual chromatographic purification steps (cf. 3.3), a radial plate diffusion test (cf. Hiemstra et al., 1993) was used.

To obtain bacteria from a logarithmic growth phase, 20 µl of a 40 ml overnight culture of *E. coli* or *Staphyloccus* aureus in 8 ml of trypticase-soy broth (TSB) was inoculated and incubated for 3.5 hours at 37° C. The bacteria were then centrifuged off for 10 minutes at 1000 g, washed with 4° C. sodium-phosphate buffer (10 mmol, pH 7.4), resuspended in 1 ml of sodium-phosphate buffer and quantified by determination of $OD_{620}$. About $1 \times 10^6$ bacteria were then added to 8 ml of preheated (42° C.) agarose medium, which consisted of 1% agarose in sodium-phosphate buffer+1% TSB medium (v/v)+0.03% Tween 80 (v/v). After feeding this agarose medium that is mixed with bacteria into a Petri dish (φ=10 cm; Sarstedt, Newton) and subsequent cooling at room temperature, holes with a 3 mm diameter were punched into the now solidified agarose layer. 5 µl of the substance in 0.01% acetic acid that was to be tested was then added to these holes.

After the incubation time was completed, the agarose layer was covered with a layer of 42° C. 2×TSB medium+1% agarose and incubated at 37° C. After about 20 to 24 hours, the inhibiting zones of the antimicrobial or antibiotic fractions could be clearly detected in the bacteria bed. The relative antimicrobial or antibiotic activities were determined by the respective diameter of the inhibiting zones.

3.3 Liquid Culture Test

To be able to assess the dose-dependent range of action of an antimicrobial or antibiotic protein, a liquid culture testing system was used (cf. Ganz et al., 1985).

About 10 µl of a $1 \times 10^7$/ml dilution of the corresponding microorganisms in sodium-phosphate buffer (cf. 3.1) was added to 80 µl of sodium-phosphate buffer together with 1.25% TSB medium (v/v). 10 µl of 0.01% acetic acid was added with the corresponding concentrations of the antimicrobial or antibiotic protein (100 µg/ml, 50 µg/ml, 25 µg/ml, 12.5 µg/ml, and 6.25 µg/ml).

These batches were incubated in a 96-hole plate (Becton Dickinson, Heidelberg) for 3 hours at 37° C. while being shaken lightly (150 rpm). After the incubation time, tenfold dilution series were made from 50 µl of each of the batches with sodium-phosphate buffer and flattened out (100 µl) in each case in 3 parallel lines on TSB-agar plates. After 24 to 36 hours of growth, the colonies were counted out.

As a control, one batch each was flattened out only with 10 µl of 0.01% acetic acid (without protein) once just before incubation and once after 2 hours of incubation at 37° C.

4. Test Results

SAP-3 was incubated at the indicated concentrations at 37° C. for 3 hours with $5 \cdot 10^4$ KBE/ml (KBE=colony-forming units) of *E. coli* and *Staphylococcus aureus* in 100 µl of 10 mmol of sodium phosphate buffer (pH=7.4) together with 1% TSB (TSB=trypticase–soy broth). The antimicrobial activity of SAP-3 was determined by counting out the KBE on the subsequent day. 100 µl of the respective batches in tenfold dilution stages was flattened out on TSB plates in advance. Then, the plates were incubated overnight at 37° C.

An $LD_{90}$ of 2.5-5 µg/ml is produced for *E. coli* and *Staphylococcus aureus* ($LD_{90}$=lethal dose of 90%; indicates the concentration range of the respective antimicrobial substances, in which the result is a 90% reduction of the colony-forming units that are used after three hours of incubation with this antimicrobial substance).

SAP-2 was incubated at the indicated concentrations at 37° C. for 3 hours with $1 \cdot 10^5$ KBE/ml of the respective microorganisms in 100 µl of 10 mmol of sodium phosphate buffer (pH=7.4) together with 1% TSB. The antimicrobial activity of SAP-2 was determined by counting out the KBE on the subsequent day. 100 µl of the respective batches was flattened out in tenfold dilution stages on TSB plates in advance. Then, the plates were incubated at 37° C. overnight.

There follows an $LD_{90}$ of 4-7.5 µg/ml for propionibacterium acnes; 7.5-15 µg/ml for *Staphylococcus aureus* and *Pseudomonas aeruginosa*; in addition 15-30 µg/ml for *Candida albicans*.

Example 5

5. Biochemical Characterization of Antimicrobial or Antibiotic Proteins with SDS-Polyacrylamide-Gel Electrophoresis (SDS-PAGE)

To determine the relative molecular weight, the tricine-SDS-polyacrylamide-gel electrophoresis was used (Schägger and Jagow, 1987), which makes it possible to separate small proteins of under 10 kDA very efficiently.

The execution took place according to the protocol of the authors (Schägger and Jagow, 1987) in a vertical gel electrophoresis chamber, whereby a 16.5% polyacrylamide gel was used with a portion of 6% bisacrylamide and 6 M urea.

The samples were denatured before the application by 0.1 M DTT and boiling up. As a molecular size marker, the standard S-17 (Sigma, St. Louis, USA) was used. After to the course of the electrophoresis, the gel was subjected to silver coloration:

First, the gel was set for 30 minutes (30% ethanol, 10% glacial acetic acid).

Then, a 30 minute incubation in "Farmer's reducer" solution was carried out.

Then, the gel was washed with HO three times for 10 minutes and colored in silver nitrate solution for 20 minutes.

Finally, a 10-15 minute incubation was carried out in developer solution.

The development was stopped by 5% acetic acid, and the gel was then photographed.

For a quick analysis of the HPLC fractions, the SDS-Page-Phast system (Pharmacia, Freiburg) was used with ready-to-use high-density gels (Pharmacia) according to information from the manufacturer. As size markers, the S-17 markers of Sigma (see above) were used. The detection of the separated molecules was carried out with the above-described silver coloration.

The invention claimed is:

1. An isolated protein, wherein said protein is an active mature protein and wherein said protein has one of the following sequences:
   a) SEQ ID NO: 1 (SAP-2); or
   b) has post-translational modifications of SEQ ID NO: 1 and said modifications do not significantly affect the activity of the active protein, wherein said activity of the active protein is antimicrobial or antibiotic activity.

2. The protein according to claim 1, which has a mobility of 6 kDa in the SDS-gel electrophoresis.

3. The protein according to claim 1, whereby protective groups are arranged at the N-terminus and/or the C-terminus.

4. The protein according to claim 1, which is a recombinant protein.

5. The protein according to claim 1 as a pharmaceutical active ingredient.

6. A pharmaceutical composition that contains one of the proteins according to claim 1 or a mixture thereof in the presence of pharmaceutically compatible and acceptable compounds and vehicles.

7. A method of treating bacterial infections in a subject in need thereof, said method comprising administering to said subject one or more of the proteins according to claim 1.

* * * * *